(12) United States Patent
Lounsberry

(10) Patent No.: US 7,366,280 B2
(45) Date of Patent: Apr. 29, 2008

(54) INTEGRATED ARC ANODE X-RAY SOURCE FOR A COMPUTED TOMOGRAPHY SYSTEM

(75) Inventor: Brian D. Lounsberry, Thiensville, WI (US)

(73) Assignee: General Electric Company, Schenectady, NY (US)

( * ) Notice: Subject to any disclaimer, the term of this patent is extended or adjusted under 35 U.S.C. 154(b) by 0 days.

(21) Appl. No.: 10/250,274

(22) Filed: Jun. 19, 2003

(65) Prior Publication Data

US 2004/0258196 A1    Dec. 23, 2004

(51) Int. Cl.
*G01N 23/00* (2006.01)
(52) U.S. Cl. .................. 378/12; 378/122; 378/143
(58) Field of Classification Search ........... 378/4–20, 378/122, 143, 146
See application file for complete search history.

(56) References Cited

U.S. PATENT DOCUMENTS

| | | | |
|---|---|---|---|
| 5,218,624 A * | 6/1993 | LeMay | 378/10 |
| 5,729,583 A * | 3/1998 | Tang et al. | 378/122 |
| 6,385,292 B1 * | 5/2002 | Dunham et al. | 378/122 |
| 6,522,721 B1 * | 2/2003 | Lustberg | 378/143 |
| 6,674,837 B1 * | 1/2004 | Taskar et al. | 378/122 |
| 6,876,724 B2 * | 4/2005 | Zhou et al. | 378/122 |
| 6,965,662 B2 * | 11/2005 | Eppler et al. | 378/25 |
| 2002/0094064 A1 * | 7/2002 | Zhou et al. | 378/122 |
| 2005/0117705 A1 * | 6/2005 | Morrison et al. | 378/136 |

* cited by examiner

*Primary Examiner*—Jurie Yun
(74) *Attorney, Agent, or Firm*—Peter Vogel, Esq.

(57) ABSTRACT

An imaging system includes a gantry rotating around an object on a table. A cathode emitter is coupled to the gantry and generates an electron beam. An anode, also coupled to the gantry, is stationary with respect to the cathode emitter and generates an x-ray flux in response to the electron beam. A detector is coupled to the gantry and is adapted to receive the x-ray flux and generate therefrom a detector signal.

20 Claims, 4 Drawing Sheets

INTEGRATED ARC ANODE X-RAY SOURCE FOR A COMPUTED TOMOGRAPHY SYSTEM

BACKGROUND OF INVENTION

The present invention relates generally to imaging systems and more particularly to volumetric computed tomography.

A computed tomography or CT scan is a method of taking pictures of the inside of the body using an ultra-thin x-ray beam. As the x-ray beam passes through the body, it is absorbed by bones, tissues and fluid within the body, thereby varying resultant beam intensity. The intensity of the attenuated x-ray beam emerging from the body is measured by a device that converts x-ray beam photons into electrical signals. These signals are converted into a detailed picture.

A typical CT scanner, such as a third or fourth generation CT scanner, includes a gantry having an annular frame for rotatably supporting an annular disk about a rotation or scanning axis of the scanner. The disk includes a central opening large enough to receive a patient extending along the scanning axis, and the disk is rotated about the patient during a scanning procedure. An x-ray tube is positioned on the disk diametrically across the central opening from an array of x-ray detectors. As the disk is rotated, the x-ray tube projects a beam of energy, or x-rays, along a scan plane, through the patient, and to the detector array. By rotating the x-ray source about the scanning axis and relative to the patient, x-rays are projected through the patient from many different directions. An image of the scanned portion of the patient is then reconstructed from data provided by the detector array using a scanner computer.

In current third and fourth generation CT systems, clinical benefits are derived from acquiring partial or whole organ volumetric images during a single rotation of the gantry. To enable this, a detector having a large (e.g. greater than 80 cm) height or "z" direction (i.e. direction parallel to the scan rotation axis) is coupled to an x-ray source having a correspondingly wide "cone beam" angle to illuminate the entire detector.

During rotation, however, image artifacts are generated that affect the system when the cone angle reaches larger ranges. Various reconstruction schemes have been devised to eliminate these artifacts, but these require the x-ray source location to vary rapidly along the "z" direction as the x-ray source is rotated around the patient. Current x-ray tubes do not have this capability.

The disadvantages associated with current, CT systems have made it apparent that a new technique for CT scanning would be beneficial.

The new technique should allow x-ray source location to vary rapidly along the "z" direction as the x-ray source is rotated around the patient.

The new technique should also substantially eliminate image artifacts that affect the system when the cone angle reaches larger ranges. The present invention is directed to these ends.

SUMMARY OF INVENTION

In accordance with one aspect of the present invention, an imaging system includes a gantry adapted to rotate. A cathode emitter is coupled to the gantry and is adapted to generate an electron beam. An anode, also coupled to the gantry, is stationary with respect to the cathode emitter and is adapted to generate an x-ray flux in response to the electron beam. A detector is coupled to the gantry and is adapted to receive the x-ray flux and generate therefrom a detector signal.

In accordance with another aspect of the present invention, a method for scanning an object includes generating a first focused electron beam from a cathode emitter and receiving the first focused electron beam in a first section of an anode. A first x-ray flux is generated therefrom. The cathode emitter is rotated around the object while the anode remains stationary, and a second focused electron beam is generated from the cathode emitter. The second focused electron beam is received in a second section of the anode, and a second x-ray flux is generated therefrom.

The present invention enables large detector volumetric imaging free from cone-beam artifacts caused through point x-ray source limitations. The present invention also addresses high speed scanning because source is not limited by anode bearing reliability as it utilizes a stationary anode. The system also provides the aforementioned scanning with 360Å° rotation coverage (in contrast to prior schemes, which were limited to "half scans").

Additional advantages and features of the present invention will become apparent from the description that follows and may be realized by the instrumentalities and combinations particularly pointed out in the appended claims, taken in conjunction with the accompanying drawings.

BRIEF DESCRIPTION OF DRAWINGS

For a more complete understanding of the invention, there will now be described some embodiments thereof, given by way of example, reference being made to the accompanying drawings, in which.

DETAILED DESCRIPTION

The present invention is illustrated with respect to a computed tomography (CT) scanning system 10, particularly suited to the medical field. The present invention is, however, applicable to various other uses that may require CT scanning, as will be understood by one skilled in the art.

Figure 1:
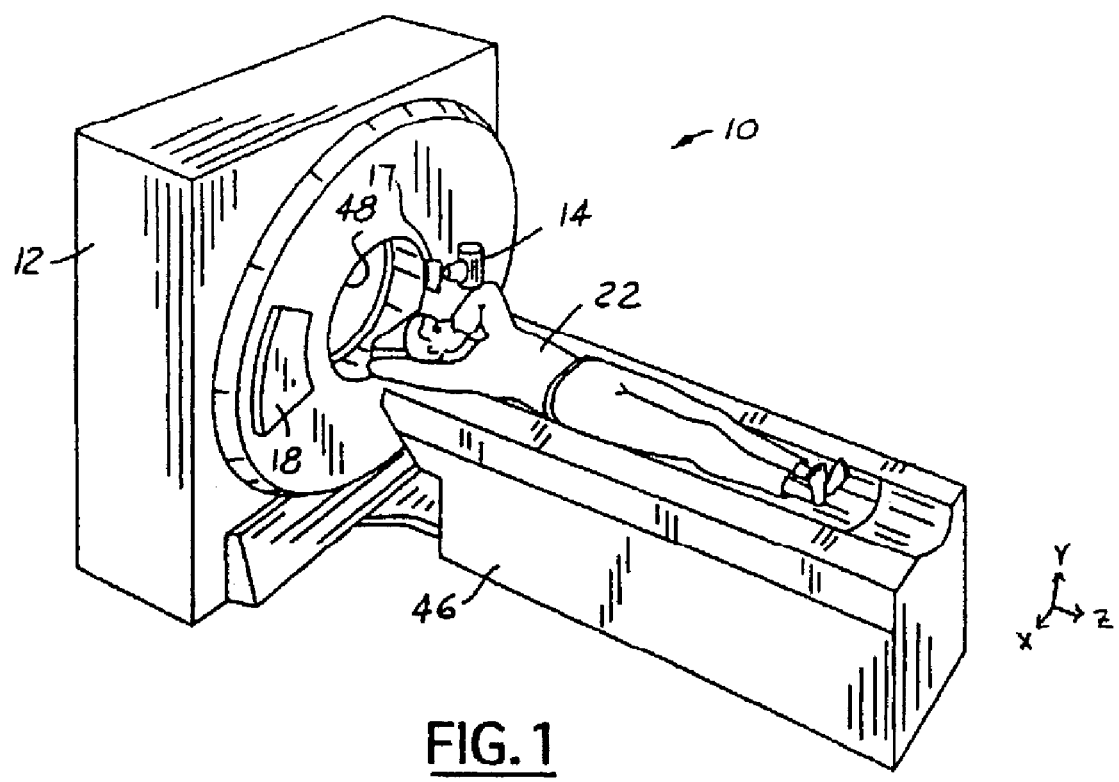
FIG. 1 is a diagram of a CT scanning system, in accordance with one embodiment of the present invention.
Figure 2:
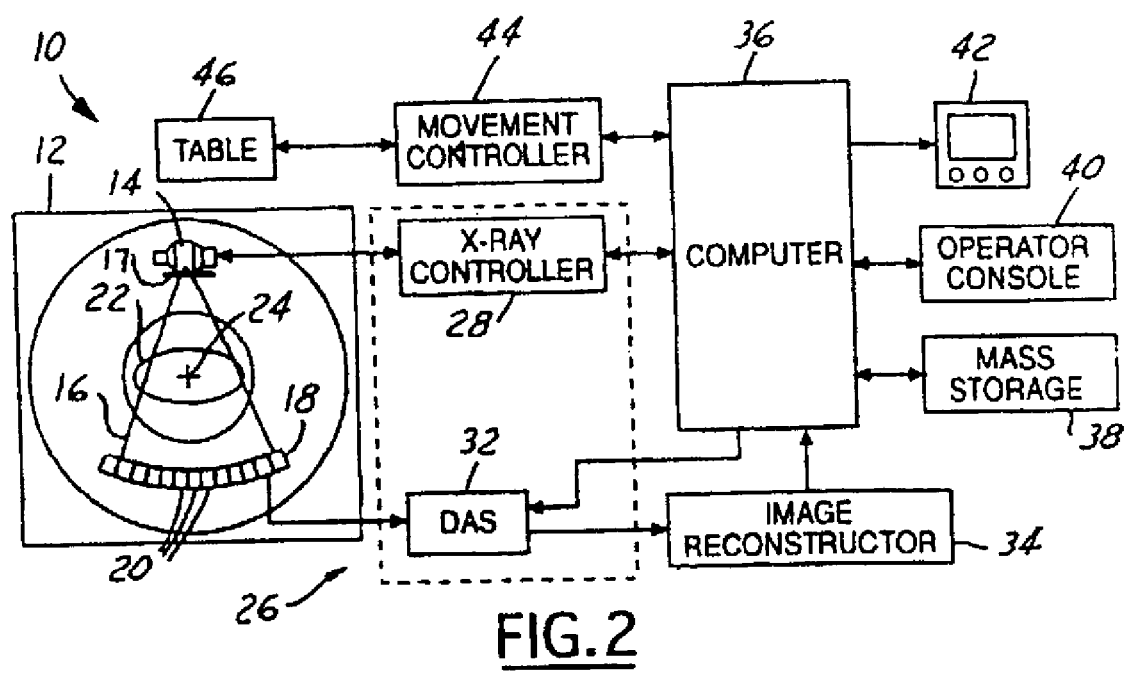
FIG. 2 is a block schematic diagram of the system illustrated in FIG. 1.

Referring to FIGS. 1 and 2, a computed tomography imaging system 10, including a gantry 12 surrounding a patient 22 on a table 46 within a patient bore 48, is illustrated. The gantry 12 has an x-ray source 14 coupled thereto that projects a beam of x-rays 16 from a stationary arc anode 17 toward a detector array 18 on the opposite side of the gantry 12.

The system 10 further includes a control mechanism 26 having an x-ray controller 32 and a data acquisition system (DAS) 32. The system 10 still further includes control components, such as a movement controller 44, a host computer 36, an operator console 40, a monitor 42, an image reconstructor 34, and a mass storage 38, all of which will be discussed later.

Within the system 10, the x-ray source 14, which is coupled to the gantry 12, includes the e-beam x-ray tube 50 and the array cathode emitter 52. The cathode emitter 52 activates and generates an electron beam, which is focused in the e-beam x-ray tube 50. The focused electron beam excites the anode surface and the anode 17 generates an x-ray flux 16. These components will be discussed further with regard to FIGS. 3 and 4.

The operation of the x-ray source 14 is governed by the control mechanism 26 of the CT system 10. The control mechanism 26 includes the x-ray controller 28 that provides power and timing signals to the x-ray source 14. The DAS 32 in the control mechanism 26 samples analog data from the detection elements 20 and converts the data to digital signals for subsequent processing. The image reconstructor 34 receives sampled and digitized x-ray data from the DAS 32 and performs high speed image reconstruction. The reconstructed image is received as an input to the computer 36 which stores the image in the mass storage device 38.

The projected x-ray flux 16, passing through the patient 22, is received in a plurality of detection elements 20 within the detector array 18. Each detection element 20 generates an electrical signal that represents the intensity of an impinging x-ray beam 16 and hence, the attenuation of the beam 16 as it passes through the patient 22.

The computer 36 also receives and supplies signals via a user interface or graphical user interface (GUI). Specifically, the computer 36 receives commands and scanning parameters from an operator console 40 that preferably includes a keyboard and mouse (not illustrated). An associated cathode emitter ray tube display 42 allows the operator to observe the reconstructed image and other data from the computer 36. The operator supplied commands and parameters are used by the computer 36 to provide control signals and information to the x-ray controller 28, the DAS 32, and the table motor controller 44, which is in communication with the table 46 to control operation of and movement of the system components.

The present invention is illustrated with respect to CT; however it is alternately used for any type of x-ray system using a detector, including: mammography, vascular x-ray imaging, bone scanning, etc. Further embodiments include non-medical applications, such as weld inspection, metal inspection, and anything that uses a digital x-ray detector to make 1, 2 or 3 dimensional images.

Figure 3:
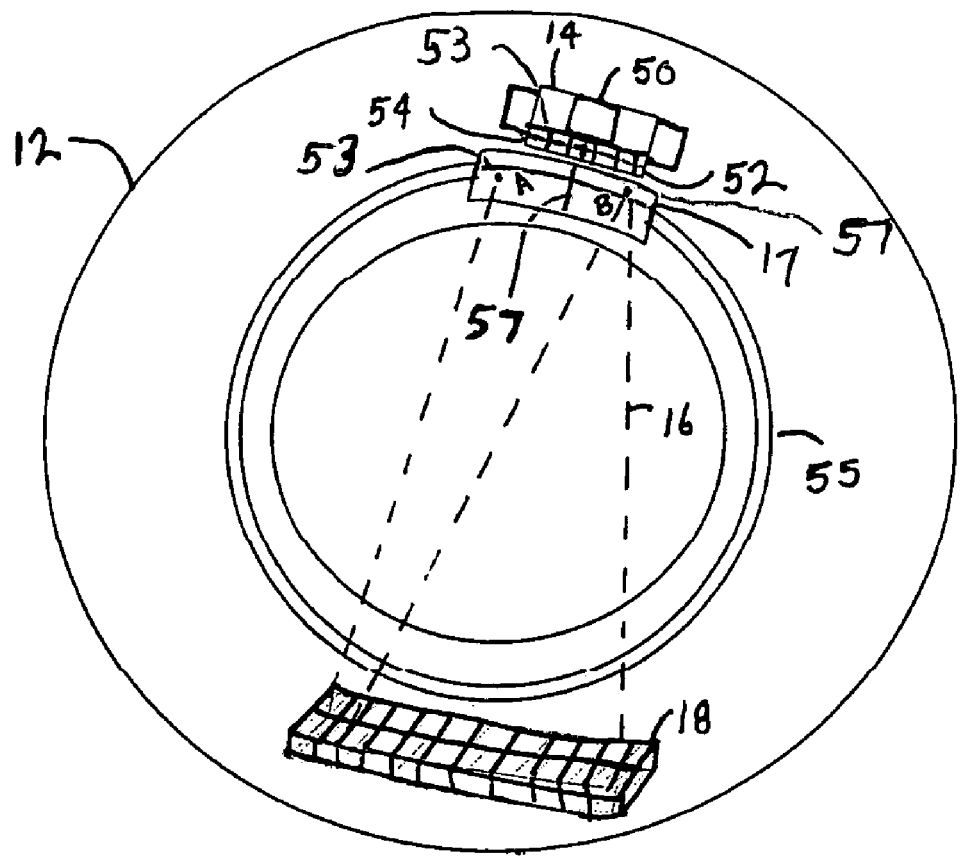
FIG. 3 is a magnified view of the x-ray scanning components of FIGS. 1 and 2.

Referring to FIG. 3, a magnified view of the x-ray scanning components and gantry 12 of FIGS. 1 and 2 is illustrated. The present invention combines the stationary arc anode used in electron beam scanners, such as the Imatron family of CT scanners, with ³rd generation rotate-rotate scanner geometry.

The array cathode emitter 52 includes field emitters 54 (numerous types known in the art are embodied herein), which may be individually addressed to generate focal spots at one or more locations on the arc anode surface at any point in time. Addressing the emitters in the tangential direction can facilitate novel image acquisition sequences for improved temporal resolution, while addressing the emitters in the axial direction permits large, rapid volume image acquisitions.

The cathode emitter 52 is coupled to the gantry 12 to allow rapid and complex focal spot motions to generate signals for various sampling schemes devised for addressing cone-beam artifacts and cardiac motion.

Regarding the latter, this type of x-ray source is ideal for situations wherein cardiac imaging with high temporal resolution is combined with gantry rotation and e-beam sweeping into a single scanner scanning over 360Â°. Alternate embodiments also include the cathode emitter 52 moveably coupled to the gantry 12 for rapid volumetric scanning.

The stationary arc anode 17 is embodied as a curved plane. The anode 17 receives cathode emitter signals and generates x-ray flux therefrom. One embodiment of the present invention includes a stationary mount 55 on which the anode 17 is mounted. Important to note is that the anode 17 is stationary with respect to the emitter 52, whereas both the emitter 52 and the anode 17 rotate with the gantry 12 during imaging sequences.

The anode 17 operates either in the x-ray transmission or reflection mode of x-ray generation.

The x-ray source 14 rotates around the patient 360Â°, and the anode 17, stationary with respect to the source 14 generates x-ray flux 16 from electron beams moving along the anode surface in the x, y, and z directions. Illustrated is x-ray flux 16 generated from different x, y, and z coordinates represented by points A and B.

Figure 4:
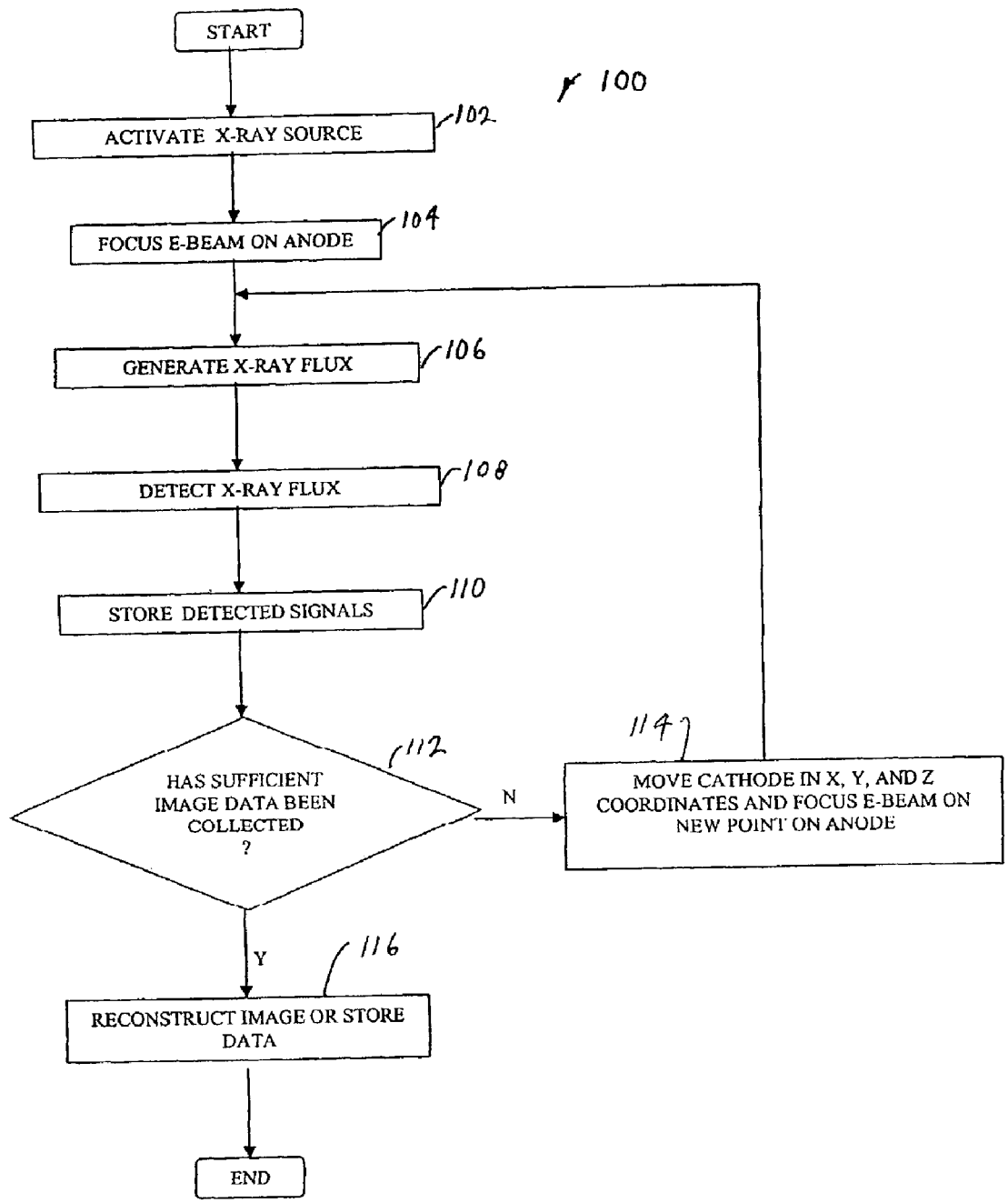
FIG. 4 is a block diagram of a method for scanning an object, in accordance with another embodiment of the present invention.

Referring to FIG. 4, a block diagram 100 of a computed tomography scanning system is illustrated. Logic starts in operation block 102 where the x-ray source 14 is activated by the host computer 36. Subsequently, in operation block 104, the x-ray source cathode emitter 52, focuses an electron beam on the anode 17.

In operation block 106, the anode 17 generates an x-ray flux from a focused electron beam on the anode surface.

In operation block 108, the x-ray flux 16 passes through a patient 22 on a table 46 and is detected by the detector 18.

In operation block 110, the detected x-ray flux 16 is acquired in the DAS 32 and is stored for future use.

In inquiry block 112, a check is made either in the host computer 36 or by a technician as to whether sufficient data has been collected to generate an image. For a negative response, operation block 114 activates, and the cathode emitter 52 is moved in at least one direction, e.g. in the x, y or z directions or any combination thereof. In other words, during a scan to acquire x-ray projection data, the gantry 12 and the components mounted thereon rotate about a central z axis. The cathode emitter 52 then focuses on a new point on the anode 17. Operation block 106 then reactivates.

Otherwise, in operation block 116, the image reconstructor 34 reconstructs an image, or the data is stored for later use in the mass storage 38.

In operation, a method for scanning an object includes generating a first focused electron beam from a cathode emitter 52 and receiving the first focused electron beam in a first section of an anode 17. A first x-ray flux 16 is generated therefrom. The cathode emitter 52 is rotated around the object. (patient 22) while the anode 17 remains stationary, and a second focused electron beam is generated from the cathode emitter 52. The second focused electron beam is received in a second section of the anode 17, and a second x-ray flux is generated therefrom.

From the foregoing, it can be seen that there has been brought to the art a new computed tomography scanning system 10 and method. It is to be understood that the preceding description of the preferred embodiment is merely illustrative of some of the many specific embodiments that represent applications of the principles of the present invention. Numerous and other arrangements would be evident to skilled in the art without departing from the scope of the invention as defined by the following claims.

The invention claimed is:

1. An imaging system comprising:
 a gantry adapted to rotate;
 a cathode emitter coupled to said gantry and adapted to generate an electron beam; said cathode emitter activating sequentially, thereby generating said beam from a sequence of points on said emitter;

an extended surface anode coupled to said gantry and stationary with respect to said cathode emitter, said extended surface anode comprising a curved planet said curved plane curved in only one direction, and adapted to generate an x-ray flux in response to said electron beam; and a detector coupled to said gantry and adapted to receive said x-ray flux and generate therefrom a detector signal.

2. The system of claim 1, wherein said cathode emitter comprises an array cathode emitter.

3. The system of claim 2, wherein said array cathode emitter comprises field emitters.

4. The system of claim 3, wherein said field emitters are adapted to focus said electronic beam at any point on said anode.

5. The system of claim 1, wherein addressing individual field emitters of said cathode emitter tangentially generates focal spots on said anode.

6. The system of claim 1, wherein addressing individual field emitters of said cathode emitter non-tangentially generates focal spots on said anode.

7. The system as in any one of claims 5 or 6, wherein said beam is deflected to various points on said anode.

8. The system of claim 1, wherein said anode is adapted to operate in x-ray transmissive mode or x-ray reflection mode or both.

9. The system of claim 1, further comprising a control mechanism adapted to receive said detector signal and generate therefrom image signals.

10. A method for scanning an object comprising:
generating a first focal spot on an arc anode comprising a curved plane, said plane curved in only one direction, from a cathode emitter; said cathode emitter activating sequentially, thereby generating only a beam from a sequence of points on said emitter;
generating a first x-ray flux as a function of said focal spot;
generating a second focal spot on a second location on said arc anode from said cathode emitter at any point in time;
generating a second x-ray flux; and
rotating said cathode emitter and said anode around said object while said arc anode remains stationary with respect to said cathode emitter.

11. The method of claim 10, further comprising generating focal spots on said anode through addressing individual field emitters of said cathode emitter tangentially.

12. The method of claim 10 further comprising generating focal spots on said anode through addressing individual field emitters of said cathode emitter non-tangentially.

13. The method as in any one of claims 11 or 12, sequentially activating said cathode emitter, thereby generating said beam from a sequence of points on said emitter.

14. The method as in any one of claims 11 or 12, further comprising deflecting said beam to various points on said anode.

15. The method of claim 11 further comprising generating an image signal from said first x-ray flux and said second x-ray flux.

16. The method of claim 10 further comprising receiving said first x-ray flux in a detector; and
receiving said second x-ray flux in said detector.

17. A computed tomography system comprising:
a gantry adapted to rotate around an object in response to signals from an imaging computer;
an x-ray source comprising an array cathode emitter, said array cathode emitter coupled to said gantry and adapted to focus on a plurality of focal spots at any point in time on an arc anode,
said arc anode comprising a curved plane, said curved plane having an arc radius of curvature around a single axis, and coupled to said gantry and stationary with respect to said array cathode emitter, said arc anode adapted to generate a first x-ray flux in response to a first one of said focal spots, said arc anode adapted to generate a second x-ray flux in response to a second one of said focal spots; and
a detector coupled to said gantry and adapted to receive said first x-ray flux and said second x-ray flux and generate therefrom a detector signals.

18. The system of claim 17, wherein said array cathode emitter comprises field emitters.

19. The system of claim 18, wherein said field emitters are adapted to focus said electronic beam at any point on said arc anode.

20. The system of claim 17, wherein said arc anode is adapted to operate in x-ray transmissive mode or x-ray reflection mode or both.

* * * * *

UNITED STATES PATENT AND TRADEMARK OFFICE
CERTIFICATE OF CORRECTION

| | |
|---|---|
| PATENT NO. | : 7,366,280 B2 |
| APPLICATION NO. | : 10/250274 |
| DATED | : April 29, 2008 |
| INVENTOR(S) | : Brian D. Lounsberry |

Page 1 of 1

It is certified that error appears in the above-identified patent and that said Letters Patent is hereby corrected as shown below:

Column 5, line 3: "planet" should read "plane"

Signed and Sealed this

First Day of June, 2010

David J. Kappos
*Director of the United States Patent and Trademark Office*